(12) United States Patent
Wolf et al.

(10) Patent No.: US 6,566,306 B1
(45) Date of Patent: May 20, 2003

(54) MICROCAPSULE FORMULATIONS

(75) Inventors: Hilmar Wolf, Langenfeld (DE); Joachim Weissmüller, Monheim (DE); Maria Giuliana Cianciulli Teller, Wuppertal (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/786,262

(22) PCT Filed: Aug. 24, 1999

(86) PCT No.: PCT/EP99/06200

§ 371 (c)(1),
(2), (4) Date: Mar. 1, 2001

(87) PCT Pub. No.: WO00/13504

PCT Pub. Date: Mar. 16, 2000

(30) Foreign Application Priority Data

Sep. 5, 1998 (DE) .......................................... 198 40 583

(51) Int. Cl.⁷ ........................ A01N 57/00; A01N 43/40; A01N 43/72; A01N 43/66; A01N 43/60

(52) U.S. Cl. ........................ 504/127; 504/128; 504/130; 504/195; 504/196; 504/223; 504/227; 504/235; 504/244

(58) Field of Search ................................ 504/359, 127, 504/128, 130, 195, 196, 223, 227, 235, 244

(56) References Cited

U.S. PATENT DOCUMENTS

| | | | |
|---|---|---|---|
| 4,181,639 A | 1/1980 | Bomer et al. | 260/29.6 WB |
| 4,253,682 A | 3/1981 | Baatz et al. | 282/27.5 |
| 5,342,556 A * | 8/1994 | Traubel et al. | 264/4.7 |
| 6,020,066 A | 2/2000 | Weisser et al. | 428/402.21 |

FOREIGN PATENT DOCUMENTS

| | | |
|---|---|---|
| DE | 1248016 | 8/1967 |
| DE | 3016189 | 10/1981 |
| EP | 0 322 820 | 7/1989 |
| EP | 0 841 088 | 5/1998 |
| GB | 2206492 | 1/1989 |
| WO | 98/29360 | 7/1998 |
| WO | 99/11122 | 3/1999 |
| WO | 00/13503 | 3/2000 |

* cited by examiner

Primary Examiner—Alton Pryor

(57) ABSTRACT

Microcapsule formulations of

A) a particulate disperse phase of
   a) a reaction product of the isocyanate of the formula

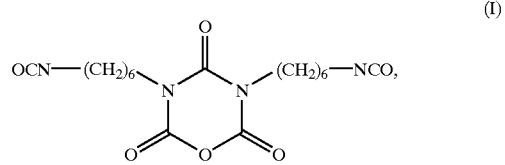

(I)

if appropriate as a mixture with toluylene diisocyanate, and
at least one diamine, polyamine, dialcohol, polyalcohol and/or aminoalcohol,
   b) at least one agrochemically active compound of a particular group of substances and,
   c) if appropriate, additives, and
B) a liquid aqueous phase, a process for the preparation of these formulations, and their use for applying the active compounds which they comprise.

13 Claims, No Drawings

MICROCAPSULE FORMULATIONS

This application is a 371 of PCT/EP99/06200 filed Aug. 24, 1999.

The present invention relates to new microcapsule formulations of agrochemically active compounds, to a process for their preparation, and to their use for applying agrochemically active compounds.

It is already known to stir agrochemically active compounds in the form of emulsifiable concentrates or wettable powders with water and to spray the plants with the resulting ready-to-use spray mixtures. The disadvantage of this method is that it is frequently very complicated to guarantee sufficient protection for the persons who apply these spray mixtures.

Furthermore, it has already been described that agrochemically active compounds can be applied in the form of aqueous microcapsule suspensions (cf. DE-A 3 016 189, DE-B 1 185 154, DE-B 1 248 016 and DE-A 2 734 577). However, it is inconvenient that such preparations often tend to agglomerate and that the active components which they contain are not always liberated in the desired quantity and over the intended prolonged period.

Finally, it can be seen from DE-A 2 738 509 that colours can be microencapsulated with the aid of 2H-1,3,5-oxadiazine-2,4,6-(3H,5H)-trione-3,5-bis-(6-isocyanato-hex-1-yl) and polyvalent amines. However, the use of the above-mentioned isocyanate for microencapsulating agrochemically active compounds have not been disclosed as yet.

There have now been found new microcapsule formulations which are composed of
A) a particulate disperse phase of
  a) a reaction product of
    2H-1,3,5-oxadiazine-2,4,6-(3H,5H)-trione-3,5-bis-(6-isocyanato-hex-1-yl), of the formula

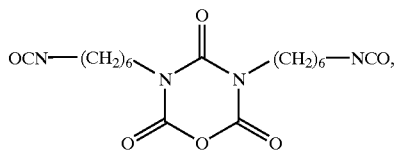

(I)

if appropriate in a mixture with toluylene diisocyanate, and
    at least one diamine, polyamine, dialcohol, polyalcohol and/or aminoalcohol,
  b) at least one fungicidally active compound from the group of the amino derivatives, the morpholine derivatives or the azole derivatives and/or
    at least one insecticidally active compound from the group of the phosphoric esters, the pyrethroids or the carbamates and/or
    at least one herbicidal active compound from the group of the acetanilides and
  c) if appropriate, additives, the particles of the disperse phase having a mean particle size of between 1 and 20 μm
B) a liquid aqueous phase.

Furthermore, it has been found that the microcapsule formulations according to the invention can be prepared by,
  α) in a first step, mixing at least one fungicidally active compound from the group of the amino derivatives, the morpholine derivatives or the azole derivatives and/or
    at least one insecticidally active compound from the group of the phosphoric esters, the pyrethroids or the carbamates and/or
    at least one herbicidally active compound from the group of the acetanilides
    with 2H-1,3,5-oxadiazine-2,4,6-(3H,5H)-trione-3,5-bis-(6-isocyanato-hex-l1-yl), of the formula

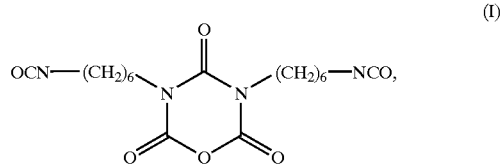

(I)

and, if appropriate, with toluylene diisocyanate
    and, if appropriate, with an organic solvent and, if appropriate, an emulsifier,
  β) then, in a second step, dispersing the resulting mixture in water, if appropriate as a mixture with additives, and,
  γ) in a third step, adding at least one diamine, polyamine, dialcohol, polyalcohol and/or aminoalcohol, if appropriate as a mixture with water and, if appropriate, additives to the resulting dispersion.

Finally, it has been found that the microcapsule formulations according to the invention are highly suitable for applying the agrochemically active compounds which they comprise to plants and/or their environment.

It is considered as extremely surprising that the microcapsule formulations according to the invention are better suited to applying the agrochemically active compounds which they contain than the constitutionally most similar prior-art preparations. What is particularly unexpected is that, amongst the large number of candidate isocyanates, it is especially 2H-1,3,5-oxadiazine-2,4,6-(3H,5H)-trione-3,5-bis-(6-isocyanato-hex-1-yl), of the formula (I), which is particularly suitable for preparing microcapsule formulations which have the desired properties.

The microcapsule formulations according to the invention are distinguished by a series of advantages. Thus, they are capable of liberating the active components over a prolonged period in the particular amount required. Another advantage is that the plant tolerance of the active compounds which they contain is improved and, moreover, that the acute toxicity of the active components is also reduced, so that applying the microcapsule formulations is unproblematic for the operator, even without major safety precautions.

The microcapsule formulations according to the invention are characterized by the components contained in the dispersed phase and in the liquid phase. 2H-1,3,5-Oxadiazine-2,4,6-(3H,5H)-trione-3,5-bis-(6-isocyanato-hex-1-yl), of the formula (I), which has been mentioned under (a) has been disclosed (cf. DE-A 2 738 509). The same applies to toluylene diisocyanate, which is also mentioned under (a).

Suitable amines of the groups mentioned under (a) are, preferably, aliphatic and alicyclic primary and secondary diamines and polyamines. Examples which may be mentioned are 1,2-ethylenediamine, diethylenetriamine, triethylenetetraamine, bis-(3-aminopropyl)-amine, bis-(2-methylaminoethyl)-methylamine, 1,4-diaminocyclohexane, 3-amino-1-methyl-aminopropane, N-methyl-bis-(3-aminopropyl)-amine, 1,4-diamino-n-butane and 1,6-diamino-n-hexane.

These diamines and polyamines are known compounds of organic chemistry.

Suitable alcohols of the groups mentioned under (a) are, preferably, primary and secondary aliphatic dialcohols and polyalcohols. Examples which may be mentioned are: ethanediol, propane-1,2-diol, propane-1,3-diol, butane-1,4-diol, pentane-1,5-diol, hexane-1,6-diol, glycerol and diethylene glycol.

These dialcohols and polyalcohols are also known.

An example which may be given of one of the aminoalcohols mentioned under (a) is triethanolamine. These aminoalcohols are also known.

The microcapsule formulations according to the invention may contain one or more of the agrochemically active compounds mentioned under (b).

Preferred fungicidally active compounds in this context are amino derivatives such as 8-(1,1-dimethylethyl)-N-ethyl-N-propyl-1,4-dioxaspiro[4,5]decane-2-methanamine (spiroxamine) and fenpropidin, and also morpholine derivatives such as aldimorph, dodemorph and fenpropimorph.

Other preferred fungicidally active compounds in the present context are triadimefon, triadimenol, bitertanol, dichlobutrazole, tebuconazole, propiconazole, difenoconazole, cyproconazole, flutriafol, hexaconazole, myclobutanil, penconazole, etaconazole, bromuconazole, epoxiconazole, fenbuconazole, tetraconazole, diniconazole, flusilazole, prochloraz, metconazole, ipconazole, fluquinconazole, triticonazole, triflumizole, imibenconazole, imazalil and 2-[2-(1-chloro-cyclo-propyl)-3-(2-chlorphenyl)-2-hydroxypropyl]-2,4-dihydro-[1,2,4]-triazole-3-thione.

Insecticidally active compounds of the groups mentioned under (b) which may preferably be mentioned are azinphos-methyl, azinphos-ethyl, bromophos A, chlorpyriphos, chlorpyriphos M, dichlorphos, edifenphos, fenamiphos, isofenphos, malathion, mesulfenphos, parathion A, parathion M, pirimiphos, profenofos, pyraclophos, tebupirimfos, betacyfluthrin, cyfluthrin, cypermethrin, trans-fluthrin und lambda-cyhalothrin, and furthermore aldicarb, aldoxycarb, aminocarb, bendiocarb, bufencarb, butacarb, butocarboxim, butoxycarboxim, 2-sec-butyl-phenyl methylcarbamate, carbanolate, carbaryl, carbofuran, cartap, decarbofuran, dimetilan, dioxacarb, ethiofencarb, fenethacarb, formetanate, formparanate, isoprocarb, methiocarb, methomyl, mexacarbate, nabam, nitrilacarb, oxamil, pirimicarb, promecarb, propoxur, thiofanox, thiocarboxim, thiram, trimethylphenyl methylcarbamate, 3,4-xylyl methylcarbamate and 3,5-xylyl methylcarbamate.

Herbicidally active compounds of the acetanilides mentioned under (b) which may preferably be mentioned are: alachlor, acetochlor, butachlor, metazachlor, metolachlor, pretilachlor and propachlor.

Suitable additives which the microcapsule formulations according to the invention may contain are organic solvents, emulsifiers, protective colloids, thickeners, preservatives, antifoams, antifreeze agents and neutralizers.

Suitable organic solvents are all customary organic solvents which, on the one hand, are sparingly miscible with water but, on the other hand, thoroughly dissolve the agrochemically active compounds employed. The following may be mentioned as being preferred: aliphatic and aromatic, optionally halogenated hydrocarbons such as toluene, xylene, Solvesso®, tetrachloromethane, chloroform, methylene chloride and dichloroethane, and furthermore also esters such as ethyl acetate.

Suitable emulsifiers.are customary surfactants which are present in formulations of agrochemically active compounds. Examples which may be mentioned are ethoxylated nonylphenols, polyethylene glycol ethers of linear alcohols, reaction products of alkylphenols with ethylene oxide and/or propylene oxide, moreover fatty acid esters, alkylsulphonates, alkyl sulphates, aryl sulphates and carboxamides such as N,N-dimethyldecanecarboxamide.

Suitable protective colloids (dispersants) are all substances which are usually employed for this purpose. The following may be mentioned as being preferred: natural and synthetic water-soluble polymers such as gelatin, starch and cellulose derivatives, in particular cellulose esters and cellulose ethers such as methylcellulose, furthermore polyvinyl alcohols, partially hydrolysed polyvinyl acetates, lignosulphonates, polyvinylpyrrolidones and polyacrylamides.

Thickeners which are suitable are all substances which can conventionally be employed for this purpose in plant treatment products. Preferred are Kelzan® (xanthan-based thixotropic thickener), silicas and attapulgite.

Suitable preservatives are all substances which are usually present in plant treatment products for this purpose. Examples which may be mentioned are Preventol® and Proxel®.

Suitable antifoams are all substances which can conventionally be employed in plant treatment products for this purpose. Silane derivatives, such as polydimethylsiloxanes, and magnesium stearate may preferably be mentioned.

Suitable substances which may act as antifreeze agents are all substances which can conventionally be used in plant treatment products for this purpose. Examples which may be mentioned are urea, glycerol and propylene glycol.

Suitable neutralizing agents are all acids and bases which are customary for this purpose. Ammonia and phosphoric acid may preferably be mentioned.

The particles of the disperse phase have a mean particle size which is generally between 1 and 20 µm, preferably between 3 and 15 µm.

The aqueous phase of the microcapsule formulations according to the invention is essentially composed of water. In addition, it may also comprise additives such as emulsifiers, protective colloids, preservatives, antifoams and antifreeze agents. Preferred components are those which have already been mentioned as being preferred for these substances. In addition, the aqueous phase may also comprise small amounts of organic solvents and of the remaining constituents of the disperse phase.

The composition of the microcapsule formulations according to the invention can be varied within a certain range. Based on the entire formulation, the disperse phase generally amounts to between 30 and 70% by weight, preferably between 40 and 60% by weight. Within the disperse phase, too, the individual components may be varied within a certain range. Thus, the concentrations in the disperse phase are as follows:

reaction product of 2H-1,3,5-oxadiazine-2,4,6-(3H,5H)-trione-3,5-bis-(6-isocyanatohex-1-yl) of the formula (I), if appropriate as a mixture with toluylene diisocyanate and diamine, polyamine, dialcohol, polyalcohol and/or aminoalcohol: generally between 1 and 12% by weight, preferably between 2 and 10% by weight, agrochemically active substances: generally between 10 and 90% by weight, preferably between 15 and 85% by weight, and additives: generally between 0 and 85% by weight, preferably between 10 and 80% by weight.

The microcapsule formulations according to the invention are prepared following the procedure for microencapsulation.

In general, a procedure is followed in which, as a first step of the process (stage α), a solution of one or more agrochemically active compounds, isocyanate of the formula (I), if appropriate as a mixture with toluylene diisocyanate and, if appropriate, organic solvent and emulsifier is preferred. If the agrochemically active compound is a solid, it is generally employed in the form of a solution in an organic solvent.

If the agrochemically active compound is liquid at room temperature, an organic solvent can be dispensed with. Preferred agrochemically active compounds, organic solvents and emulsifiers are those which have already been mentioned in connection with the description of the microcapsule formulations according to the invention as being preferred.

The quantities of the individual components are chosen in such a way that they are present, in the resulting disperse phase, in those concentrations which have already been mentioned as being preferred. The ratio of isocyanate of the formula (I) to toluylene diisocyanate may be varied within a certain ratio. In general, between 0 and 10 parts by weight, preferably between 0 and 5 parts by weight, of toluylene diisocyanate are employed per part by weight of isocyanate of the formula (I).

The solution prepared in stage α of the process according to the invention is dispersed in the second step of the process (stage β) in water, if appropriate as a mixture with additives.

Suitable additives are protective colloids and emulsifiers. Preferably suitable are those substances which have already been mentioned in connection with the description of the microcapsule formulations according to the invention as being preferred protective colloids or emulsifiers.

To prepare the dispersions, all devices which are suitable for such purposes and which produce potent shearing forces may be employed. Examples which may be mentioned are rotor/stator mixers and jet dispersing machines.

The dispersion prepared in stage β of the process according to the invention is treated in the third step of the process (stage γ) while stirring first with at least one diamine, polyamine, dialcohol, polyalcohol and/or aminoalcohol and, if appropriate, also with additives after the reaction which starts has ended.

Suitable reactants are preferably all those diamines, polyamines, dialcohols, polyalcohols and aminoalcohols which have already been mentioned as being preferred in connection with the description of the microcapsule formulations according to the invention.

Suitable additives for carrying out stage γ of the process according to the invention are thickeners, preservatives, antifoams and antifreeze agents. Those substances which have already been mentioned in connection with the description of the microcapsule formulations according to the invention as being preferred thickeners, preservatives, antifoams and antifreeze agents can preferably be used.

When carrying out the process according to the invention, the ratio of isocyanate to amine, or alcohol, components can be varied within a certain range. In general, 0.8 to 1.5 equivalents of amine, or alcohol, component are employed per mole of isocyanate. The quantities of isocyanate and amine, or alcohol, are preferably chosen in such a way that equimolar amounts of isocyanate groups and amino, or hydroxyl, groups are present.

When carrying out the process according to the invention, the reaction temperatures can be varied with a certain range. The process is generally carried out, when carrying out the first step, at temperatures between 0° C. and 40° C., preferably between 2° C. and 30° C., when carrying out the second step, at temperatures between −10° C. and +40° C., preferably between 0° C. and 30° C. and when carrying out the third step, at temperatures between 0° C. and 80° C., preferably between 10° C. and 75° C.

The process according to the invention is generally carried out under atmospheric pressure.

The microcapsule formulations according to the invention are outstandingly suited for applying the agrochemically active compounds which they contain to plants and/or their environment. They ensure liberation of the active components in the specific quantity desired over a prolonged period.

The microcapsule formulations according to invention can be employed in practice either as such or after previous dilution with water. They are applied by the customary methods, for example by pouring, spraying or atomizing.

The application rate of the microcapsule formulations according to the invention can be varied within a substantial range. It depends on the agrochemically active compounds in question and on their content in the microcapsule formulations.

The invention is illustrated by the examples which follow.

PREPARATION EXAMPLES

Example 1

A solution of 75.8 g of fenarniphos, 45.3 g of Solvesso® 200, 1.8 g of 2H-1,3,5-oxadiazine-2,4,6-(3H,5H)-trione-3,5-bis-(6-isocyanato-hex-1-yl) and 3 g of toluylene diisocyanate is dispersed at 25° C. with the aid of a dispersing machine at 11 500 rotations per minute in the course of one minute in 140.3 g of a 1% by weight solution of polyvinyl alcohol (Mowiol 26-88®) in water in a mixture with 0.06 g of silicone antifoam. 3 g of a 50% by weight solution of diethylenetriamine in water are then added. The resulting reaction mixture is heated to 70° C. in the course of 2 hours and then held at 70° C. for a further 4 hours, with gentle stirring. After the mixture has subsequently cooled to room temperature, 30 g of a 2% by weight solution of Kelzan S (xanthan-based thickener) in water and 0.54 of preservative (Preventol® D7) are added. This gives 300 g of a microcapsule formulation with a fenamiphos content of 240 g/l and a mean particle size of 6.6 μm.

Example 2

A solution of 126.4 g of fenamiphos, 73.6 g of Solvesso® 200, 4.6 g of 2H-1,3,5-oxadiazine-2,4,6-(3H,5H)-trione-3,5-bis-(6-isocyanato-hex-1-yl) and 3.9 g of toluylene diisocyanate is dispersed at 25° C. with the aid of a dispersing machine at 6000 rotations per minute in the course of one minute in 236.8 g of a 1% by weight solution of polyvinyl alcohol (Mowiol 26-88®) in water in a mixture with 0.1 g of silicone antifoam. 4.6 g of a 50% by weight solution of diethylenetriamine in water are then added. The resulting reaction mixture is heated to 70° C. in the course of 2 hours and then held at 70° C. for a further 4 hours, with gentle stirring. After the mixture has subsequently cooled to room temperature, 50 g of a 2% by weight solution of Kelzan S (xanthan-based thickener) in water and 0.9 of preservative (Preventol® D7) are added. This gives 500 g of a microcapsule formulation with a fenamiphos content of 240 g/l and a mean particle size of 5.0 μm.

Example 3

A solution of 1955 g of spiroxamine, 145 g of xylene and 227 g of 2H-1,3,5-oxadiazine-2,4,6-(3H,5H)-trione-3,5-bis-(6-isocyanato-hex-1-nyl) is dispersed at 2° C. with the aid of a dispersing machine at 8000 rotations per minute in the course of 3 minutes in 3017 g of a 1% by weight solution of polyvinyl alcohol (Mowiol 26-88®) in water. 205 g of a 20% by weight solution of diethylenetriamine in water are then added in the course of 2 minutes. The resulting reaction mixture is heated at 55° C. for 4 hours, with stirring. After the mixture has subsequently cooled to room temperature, 450 g of a 2% by weight solution of Kelzan S (xanthan-based thickener) are added. The pH of the formulation is brought to 7 by addition of 25% aqueous ammonia solution. This gives a microcapsule formulation with a spiroxamine content of 300 g/l.

Example 4

A solution of 123.33 g of fenpropidin, 27.48 g of N,N-dimethyldecanecarboxamide and 15.18 g of 2H-1,3,5-oxadiazine-2,4,6-(3H,5H)-trione-3,5-bis-(6-isocyanato-hex-1-yl) is dispersed at 15° C. with the aid of a dispersing machine at 8000 rotations per minute in the course of 30 seconds in 376 g of a 1% by weight solution of polyvinyl alcohol (Mowiol 26-88®) in water. 13.02 g of a 20% by weight solution of diethylene-triamine in water are then added in the course of 2 minutes with gentle stirring. The resulting reaction mixture is heated for 4 hours at 55° C. and stirring is continued. Thereafter, 1.4 ml of a 25% aqueous ammonia solution are added, and the mixture is stirred for a further 30 minutes at 55° C. It is then cooled to room temperature, the pH is brought to 7 by addition of concentrated phosphoric acid, and 45 g of a 2% by weight solution of Kelzan S (xanthan-based thickener) are added. This gives a microcapsule formulation with a fenpropidin content of 200 g/l.

Example 5

A mixture of 180.0 g of tebupirimphos and 9.1 g of 2H-1,3,5-oxadiazine-2,4,6-(3H,5H)-trione-3,5-bis-(6-isocyanato-hex-1-yl) is dispersed at 9–11° C. with the aid of dispersing machine at 8000 rpm in 245.5 g of a 1% by weight solution of polyvinyl alcohol (Mowiol 26-880®) in a mixture with 0.1 g of a silicone antifoam. 15.3 g of a 10% by weight solution of diethylene-triamine in water are then added. The resulting reaction mixture is heated to 55° C. in the course of 2 hours and then held at 55° C. for a further 4 hours with gentle stirring. After the mixture has subsequently cooled to room temperature, 50 g of a 40% by weight solution of polyethylene glycol in water are added. This gives 500 g of a microcapsule formulation with a tebupirimphos content of 360 g/l and a mean particle size of 8.0 μm.

Example 6

A solution of 30.3 g of β-cyfluthrin, 89.9 g of Solvesso 200®, 0.24 g of tristyryl-phenol ethoxylate, 0.58 g of toluylene diisocyanate and 0.34 of 2H-1,3,5-oxadiazine-2,4,6-(3H,5H)-trione-3,5-bis-(6-isocyanato-hex-1-yl) is dispersed at 15° C. with the aid of a dispersing machine at 10 000 rpm in the course of one minute in 147.4 g of a 1% by weight solution of polyvinyl alcohol (Mowiol 26-880®) in water in a mixture with 0.06 g of a silicone antifoam. 0.57 g of a 50% by weight solution of diethylene-triamine in water are then added. The resulting reaction mixture is heated to 70° C. in the course of one hour and held for a further 4 hours at 70° C., with gentle stirring. After the mixture has subsequently cooled to room temperature, 30.0 g of a 2% by weight solution of Kelzan S® (xanthan-based thickener) in water and 0.54 g of preservative (Preventol® D7) are added. This gives 300 g of a microcapsule formulation with a β-cyfluthrin content of 100 g/l and a mean particle size of 4.7 μm.

Use Example

To check the release of active compound, in each case 3 g of a microcapsule formulation are suspended in 1 liter of water and the suspension is stirred for 48 hours at room temperature. Then, 5-ml-samples are taken and centrifuged to separate the microcapsules. The active compound content in the remaining aqueous phase is determined by HPLC.

The results can be seen from the table which follows.

TABLE 1

| Example No. | Active compound content |
|---|---|
| 1 | 117 ppm |
| 2 | 26 ppm |

What is claimed is:
1. A microcapsule formulation having a particulate disperse phase and a liquid aqueous phase comprising:
A) a particulate disperse phase consisting essentially of components (a), (b) and (c), wherein
a) said component (a) is a reaction product of 2H-1,3,5-oxadiazine-2,4,6-(3H,5)-trione-3,5-bis-(6-isocyanato-hex-1-yl), of the formula

(I)

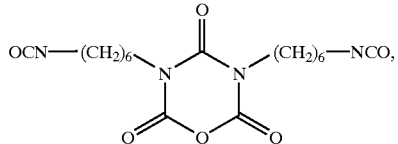

with
a compound selected from the group consisting of 1,2-ethylenediamine, diethylenetriamine, triethylenetetraamine, bis-(3-aminopropylyamine, bis-(2-methylaminoethyl)-methylamine, 1,4-diamino-cyclohexane, 3-amino-1-methyl-aminopropane, N-methyl-bis-(3-aminopropyl)-amine, 1,4-diamino-n-butane, 1,6-diamino-n-hexane, ethanediol, propane-1,2-diol, propane-1,3-diol, butane-1,4-diol, pentane-1,5-diol, hexane-1,6-diol, glycerol and diethylene glycol,
and optionally, toluene diisocynate,
b) said component (b) is selected from the group consisting of a fungicidally active compound, an insecticidally active compound, a herbicidally active compound, and combinations thereof, wherein
said fungicidally active compound is selected from the group consisting of an amino-based fungicidally active compound, a mopholine-based fungicidally active compound, an azole-based fungicidally active compound and combinations thereof
said insecticidally active compound is selected from the group consisting of a phosphoric ester, a pyrethroid, a carbamate and combinations thereof
said herbicidally active compound is an acetanilide, and
c) said component (c) is an additive selected from the group consisting of organic solvents, emulsifiers, protective colloids, thickeners, preservatives, antifoams, antifreeze agents and neutralizers,
wherein the particles of said particulate disperse phase have a mean particle size of between 1 and 20 μm,
and
B) a liquid aqueous phase,
in which microcapsule formulation the weight ratio of said particulate disperse phase (A) to said liquid aqueous phase (B) is between 40:60 and 60:40.

2. A microcapsule formulation according to claim 1, wherein the fungicidally active compound is spiroxamine.

3. A microcapsule formulation according to claim 1, wherein the fungicidally active compound is fenpropidin.

4. A microcapsule formulation according to claim 1, wherein the insecticidally active compound is fenamiphos.

5. A microcapsule formulation according to claim 1, wherein the insecticidally active compound is tebupirimfos.

6. A microcapsule formulation according to claim 1, wherein the insecticidally active compound is cyfluthrin.

7. A microcapsule formulation according to claim 1, wherein the insecticidally active compound is beta-cyfluthrin.

8. A process for the preparation of a microcapsule formulation according to claim 1, which in the process comprises α) mixing in a first step one or more compounds selected from the group consisting of a fungicidally active compound, an insecticidally active compound, a herbicidally active compound and combinations thereof, wherein
said fungicidally active compound is selected from the group consisting of an amino-based fungicidally active compound, a morpholine-based fungicidally active compound, an azole-based fungicidally active compound and combinations thereof,
said insecticidally active compound is from the group consisting of a phosphoric ester, a pyrethroid, a carbamate and combinations thereof;
said herbicidally active compound is an acetanilide with
2H-1,3,5-oxadiazine-2,4,6-(3H,5H)-trione-3,5-bis-(6-isocyanato-hex-1-yl), of the formula $$\text{OCN—(CH}_2)_6\text{—N}\underset{\underset{\text{O}}{|}}{\overset{\overset{\text{O}}{||}}{\text{C}}}\text{N—(CH}_2)_6\text{—NCO,} \quad (I)$$

and, optionally with,
toluene diisocyanate,
wherein said mixing step optionally occurs in an organic solvent and optionally with an emulsifier, said mixing step being carried out at a temperature between 0° C. and 40° C., β) then, in a second step, dispersing the resulting mixture from said step (α) in water, optionally with an additive, said dispersing step being carried out at a temperature between −100° C. and +40° C. to form a dispersion, and γ) in a third step, adding to the resulting dispersion of said second step (β), a compound selected from the group consisting of 1,2-ethylenediamine, diethylenetriamine, triethylenetetraamine, bis-(3-aminopropyl)-amine, bis-(2-methylaminoethyl)methylamine, 1,4-diamino-cyclohexane, 3-amino-1-methyl-aminopropane, N-methyl-bis-(3-aminopropylyamine, 1,4-diamino-n-butane, 1,6-diamino-n-hexane, ethanediol, propane-1,2-diol, propane-1,3-diol, butane-1,4-diol, pentane-1,5-diol, hexane-1,6-diol, glycerol and diethylene glycol, wherein said compound of said third step (γ) is optionally mixed with water and/or is optionally mixed with an additive, said third adding step being carried out at a temperature between 0° C. and 80° C., in which process 0.8 to 1.5 equivalents of amine or alcohol component are employed per mole of isocyanate.

9. A process for applying agrochemically active compounds to plants comprising applying an effective amount of the microcapsule formulation of claim 1 to said plants and/or their environment.

10. A microcapsule formulation according to claim 1, wherein the component (a) is a reaction product of
2H-1,3,5-oxadiazine-2,4,6-(3H ,5H)-trione-3,5-bis-(6-isocyanato-hex-1-yl), of the formula $$\text{OCN—(CH}_2)_6\text{—N}\underset{\underset{\text{O}}{|}}{\overset{\overset{\text{O}}{||}}{\text{C}}}\text{N—(CH}_2)_6\text{—NCO,} \quad (I)$$

and
tolulenediisocyanate
with a compound selected from the group consisting of 1,2-ethylenediamine, diethylenetriamine, triethylenetetraamine, bis-(3-aminopropyl)-amine, bis-(2-methylaminoethyl)-methylamine, 1,4-diamino-cyclohexane, 3-amino-i-methyl-aminopropane, N-methyl-bis-(3-aminopropyl)-amine, 1,4-diamino-n-butane, 1,6-diamino-n-hexane, ethanediol, propane-1,2-diol, propane-1,3-diol, butane-1,4-diol, pentane-1,5-diol, hexane-1,6-diol, glycerol and diethylene glycol.

11. The microcapsule formulation of claims 1, 8 or 10, wherein said fungicidally active compound is selected from the group consisting of 8-(1,1-dimethylethyl)-N-ethyl-N-propyl-1,4-dioxaspiro[4,5]decane-2-methanamine (spiroxamine), fenpropidin, aldimorph, dodemorph, fenpropimorph, triadimefon, triadimenol, bitertanol, dichlobutrazole, tebuconazole, propiconazole, difenoconazole, cyproconazole, flutriafol, hexaconazole, myclobutanil, penconazole, etaconazole, bromuconazole, epoxiconazole, fenbuconazole, tetraconazole, diniconazole, flusilazole, prochloraz, metconazole, ipconazole, fluquinconazole, triticonazole, triflumizole, imibenconazole, imazalil and 2-[2-(1-chloro-cyclo-propyl)-3-(2-chlorophenyl)-2-hydroxypropyl]-2,4-dihydro-[1,2,4]-triazole-3-thione.

12. The microcapsule formulation of claims 1, 8 or 10, wherein said insecticidally active compounds are selected from the group consisting of azinphos-methyl, azinphos-ethyl, bromophos A, chlorpyriphos, chlorpyriphos M, dichlorphos, edifenphos, fenamiphos, isofenphos, malathion, mesulfenphos, parathion A, parathion M, pirimiphos, profenofos, pyraclophos, tebupirimfos, betacyfluthrin, cyfluthrin, cypermethrin, transfluthrin und lambda-cyhalothrin, aldicarb, aldoxycarb, aminocarb, bendiocarb, bufencarb, butacarb, butocarboxim, butoxycarboxim, 2-sec-butyl-phenyl methylcarbamate, carbanolate, carbaryl, carbofuran, cartap, decarbofuran, dimetilan, dioxacarb, ethiofencarb, fenethacarb, formetanate, formparanate, isoprocarb, methiocarb, methomyl, mexacarbate, nabam, nitrilacarb, oxamil, pirimicarb, promecarb, propoxur, thiofanox, thiocarboxim, thiram, trimethylphenyl methylcarbamate, 3,4-xylyl methylcarbamate and 3,5-xylyl methylcarbamate.

13. The microcapsule formulation of claims 1, 8 or 10, wherein said herbicidally active compound is selected from the group consisting of alachlor, acetochlor, butachlor, metazachlor, metolachlor, pretilachlor and propachlor.

* * * * *